United States Patent
Libin

(10) Patent No.: US 6,440,395 B1
(45) Date of Patent: *Aug. 27, 2002

(54) ANTIPLAQUE MOUTH RINSE

(76) Inventor: Barry M. Libin, 15 Thornhedge Rd., Bellport, NY (US) 11713

(*) Notice: Subject to any disclaimer, the term of this patent is extended or adjusted under 35 U.S.C. 154(b) by 0 days.

This patent is subject to a terminal disclaimer.

(21) Appl. No.: 09/168,950

(22) Filed: Oct. 9, 1998

Related U.S. Application Data

(63) Continuation of application No. 08/051,861, filed on Apr. 26, 1993, now abandoned, which is a division of application No. 07/901,679, filed on Jun. 22, 1992, now Pat. No. 5,236,699, which is a continuation-in-part of application No. 08/798,504, filed on Feb. 10, 1997, now abandoned.

(51) Int. Cl.$^7$ ............................ A61K 7/16; A61K 7/22

(52) U.S. Cl. ......................................... 424/49; 424/54

(58) Field of Search ..................... 424/49–58

(56) References Cited

U.S. PATENT DOCUMENTS

| | | |
|---|---|---|
| 2,921,885 A | 1/1960 | Bouchal |
| 4,022,880 A | 5/1977 | Vinson et al. |
| 4,098,877 A | 7/1978 | Ball et al. |
| 4,111,844 A | 9/1978 | Polony et al. |
| 4,205,061 A | 5/1980 | Vidra |
| 5,154,917 A | 10/1992 | Ibrahim et al. |
| 5,185,377 A | 2/1993 | Schewe et al. ............ 514/721 |
| 5,188,820 A | 2/1993 | Cummins et al. |
| 5,236,599 A | 8/1993 | Libin |
| 5,286,492 A | 2/1994 | Dettmar et al. |
| 5,492,937 A | 2/1996 | Bogentoft et al. .......... 514/781 |
| 5,549,885 A | 8/1996 | Torchinsky ................. 424/54 |
| 5,855,872 A | 1/1999 | Libin |

FOREIGN PATENT DOCUMENTS

| | | |
|---|---|---|
| EP | 396 317 | 11/1990 |
| EP | 0455475 | 11/1991 |
| EP | 0528468 | 2/1993 |
| EP | 549 267 | 6/1993 |
| EP | 95/17159 | 6/1995 |
| EP | 679 390 | 11/1995 |
| FR | 2 335 203 | 12/1975 |
| GB | 2207604 | 2/1989 |
| WO | 91/15189 | 10/1991 |
| WO | 92/20319 | 11/1992 |
| WO | 9325209 | 12/1993 |

OTHER PUBLICATIONS

Jenkins et al III JL. Clin. Periodontol 21(6): 441–444 comparative Plaque Regrowth Effects of MW of T/CPC/CHX, 1994.*
Jenkins et al IV JL. Clin. Periodontol. 21(6): 397–401 Salivary Bacterial Counts to Measure Magnitude, Duration A T MW is CHX MN. vs CPC M–W 1994.*
Van Der Hoeven Caries Res. 27(4): 298–302 Comparison of Dental Plaque Acid Reduction by MW of CHX vs. MW of T and ZN (CHX MW Stasticaly Significan), 1993.*
Ramburg. Peterl JL. Clinical Periodontol 7:509–520 De Novo Plaque Formation Reduction Comparisons of MW T vs. AW of CHX, Aug. 1992.*
Pratten et al J. Appl. Microbiol. 84(6): 1149–1155 Comparisons of S. Sangui Biofilm Inhibition From Mouthwashes of Each of: T/CHX/CPC, 1998.*
Thrower et al J. Med. Microbiology 46(5): 425–429 Comparisons of Actinobacillus Biofilm Inbibition From Mouthwases of Each of : T, CHX, CPC, 1997.*
Bouwsma Curr Opinion in Periodontology 3 : 78–84 pp 81–82 Reviews 4 Day Plaque Regrowth Models Comparing T, CPC and CHX. (CPC/CHX Always More Effective than T), 1996.*
Renton Harper et al J. Periodontol–67(5): 486–489 Comparison of Plaque Inhibition of MW of T, CPC, CHX, 1996.*
Kjasheim European JL. of Oral Sciences 103(3): 179–181 2 Phase Mouthrinse of 0.3% T, 0.2% CHX Oil Phase Aqueous Phase (No Added Effect of 2 Phase or 1 Phase MW) Jun. 1995
Jones JL. of Drug Targeting 5(1):25–34 Biofilm Oral Bacteria (S. Mutans) (S. Janguinvis) Inhibited by Liposomes Delivering T (Oil–Soluble) and CHX (Water Soluble) Both Bactericides, 1997.
Lurya et al Pharmaceutical Research 14(11) ; Suppl. p. S720 Antiseptic Oral Rinse of T and CHX in Bioadhesive Mixed Micelles to Oral Cavity Mucosal Surfaces, Nov. 1997.
Jenkins et al (I) J. Clin. Periodontol 18(2):140–144 A Single Mouth Rinse of 0.2% T, 0.2% CHX, 1% SLS, Feb. 1991.
Jenkins S et al. (II) J. Clin. Periodontol 18(2):145–148 A Single Mouth Rinse of 0.2% T, 0.2% CHX, 1% SLS, Feb. 1991.
Roella et al Arch. Oral. Biol. 16(9):1109–1116 0.2% CHX M.W. is Absorbed on Mucous Membranes Plaque Tooth and Pellicle Surfaces. Salivary Bacteria Count 2 Hrs After Rinsing, 1971.
Skaare et al J. Clin. Periodontol 23(12):1100–1103 The Antibacterial Triclosan May Have Anti–Inflammatory Properties on SLS Inflamed Mucous Membranes Gingiva, 1996.
Computer Print Out, Dated 1998.

(List continued on next page.)

Primary Examiner—Shep K. Rose
(74) Attorney, Agent, or Firm—Hedman & Costigan, P.C.

(57) ABSTRACT

An antiplaque mouth rinse conducive to oral hygiene. The mouth rinse composition includes a water-alcohol vehicle having dissolved therein two antibacterial agents that coact to promote the delivery of these agents and their retention on the teeth and soft tissue in the dental region of the oral cavity of the user, thereby inhibiting the formation of plaque. One agent, Triclosan, is water-insoluble and noncationic, a solubilizer therefor being included in the composition. The other agent, cetyl pyridinium chloride (CPC) is soluble in water and alcohol and is cationic. When the combination of Triclosan and CPC is delivered to the dental region, it is adsorbed and retained thereby to afford enhanced antibacterial activity.

6 Claims, No Drawings

OTHER PUBLICATIONS

Letter from Sharon F. Suer of Oct. 22, 1998, Computer Print Out Dialog Re: Apr. 1993 Publication of IMS Word Files.

Letter from Andy Ingram of IMS World, Dated Oct. 22, 1998.

Letter from IMS Health to Linda Raffensberger with attached page of New Product Launch, Letter dated Mar. 30, 1992.

Min. Stom., 28, 1979, pp. 209–213.

J. Dental Research, 68, pp. 1706–1707 (1989).

* cited by examiner

ANTIPLAQUE MOUTH RINSE

This application is a continuation of Ser. No. 08/051,861, filed Apr. 26, 1993, now abandoned which is a divisional application of Ser. No. 07/901,679, filed Jun. 22, 1992, now U.S. Pat. No. 5,236,699 and is related to Ser. No. 08/934,327, filed Sep. 19, 1997, now, U.S. Pat. No. 5,855,872, which is a continuation-in-part of Ser. No. 08/798,504, filed Feb. 10, 1997, now abandoned which is a continuation-in-part of Ser. No. 08/051,861 filed Apr. 26, 1993, abandoned which is a divisional of Ser. No. 07/901,679, filed Jun. 22, 1992, now U.S. Pat. No. 5,236,699 and is also related to Ser. No. 09/224,972, filed Jan. 4, 1999, now abandoned; Ser. No. 09/224,781, pending filed Jan. 4, 1999 and Ser. No. 09/167,225, pending filed Oct. 6, 1998 and Ser. No. 09/186,825, filed Nov. 5, 1998, now U.S. Pat. No. 5,945,089.

BACKGROUND OF INVENTION

1. Field of the Invention

This invention relates generally to antiplaque mouth rinses conducive to oral hygiene, and more particularly to a mouth rinse whose formulation includes two antibacterial agents: Triclosan and cetyl pyridinium chloride. These coact to promote the delivery and retention of these agents on the teeth and soft tissue in the dental region of the oral cavity of the user to provide enhanced bacterial activity inhibiting the development of plaque.

2. Status of Prior Art

Dental plaque is a mucous film that harbors bacteria on the teeth. Calculus or tartar is an encrustation on the teeth consisting of salivary secretions, food residues and various salts, such as calcium phosphate. Dental plaque, a precursor of calculus, unlike calculus may form on any part of the tooth surface, including the gingival margin; hence it is implicated in the occurrence of gingivitis and periodontal disease.

It is generally acknowledged in dentistry that plaque which contains a combination of pathogenic microorganisms is a principal etiological factor associated with periodontal disease, dental infections and caries. The usual approach toward combating plaque is by mechanical expedients, such as toothbrushing, dental floss and toothpicks. However, even the most thorough tooth cleaning fails to eliminate interproximal plaque, yet it is the plaque lodging between adjacent teeth that plays a major role in periodontal disease. It therefore becomes necessary to complement mechanical oral hygiene measures with chemotherapeutic agents to inhibit the development of plaque.

Among the many chemotherapeutic agents heretofore used in inhibiting dental plaque are cationic agents such as chlorhexidine. However, there are major drawbacks associated with the use of this agent; for it not only has an unpleasant taste, but it also results in staining of the teeth and tongue.

Cethyl pyridinium chloride (CPC) is another cationic agent that has been formulated into various mouth rinse products. This antiseptic is usually used in a concentration ranging from 0.05 to 0.10% in mouth rinses. Yet as noted by Moran and Addy in J. Periodontol 1991; 62:562–562, "The Effects of a Cetylpyridinium Chloride Prebrushing Rinse as an Adjunct to Oral Hygiene and Gingival Health," there seems to be general agreement that CPC mouth rinses are effective but not as effective against plaque and gingivitis as chlorhexidine, although the use of CPC does not result in significant dental staining.

Also known to be effective against plaque is Triclosan, an antibacterial agent. In the article by Gjermo and Saxton, Antibacterial Dentifrices" appearing in J. Clin. Periodontal 1991: 18: 468–473, it is noted that several studies indicate that Triclosan alone, in spite of its broad antibacterial spectrum, has only a moderate effect on plaque formation. While Triclosan has been shown to be retained in plaque for several hours, the salivary release curve is relatively steep, thereby indicating a rapid release from oral binding sites. On the other hand, when Triclosan is incorporated in a copolymer which is retained on oral surfaces, it then provides the oral cavity with a reservoir of Triclosan. However, the copolymer makes no contribution to combating plaque.

As indicated in the Gaffar et al. patent, 5,043,154, cationic antibacterial materials such as chlorhexidine and CPC have been the subject of many investigations as antibacterial agents. Nevertheless, in spite of the fact that these cationic agents have been used in conjunction with zinc salt acting as an anticalculus agent, they have not been found to be effective when-used with anionic materials, such as a polyphosphate anticalculus agent.

In the oral composition disclosed in the Gaffar et al. patent '154, the mouth wash formulation includes a water-soluble polyphosphate salt as an anticalculus agent in combination with the water-insoluble noncationic antibacterial compound Triclosan, acting as an antiplaque agent. Triclosan is 2,4,4'-trichloro-2'-hydroxydiphenyl ether.

The antibacterial composition disclosed in the Nabi et al. U.S. Pat. Nos. 4,894,220 and 5,037,635 for use as a dentifrice or mouth wash contains water and includes Triclosan, a substantially water-insoluble noncationic antiplaque agent as well as a solubilizer therefor, such as propylene glycol. The formulation further includes a synthetic anionic linear polymeric polycarboxylate having a molecular weight of about 1000 to about 1,000,000. The anionic polymeric agent is said to enhance the delivery and retention of the antibacterial agent on teeth and on soft oral tissue. But this polymeric agent lacks antibacterial properties and does not itself act to retard the growth of plaque, even though it is retained in the dental region.

In the Gaffar et al. U.S. Pat. No. 5,037,637, there is disclosed an oral composition such as a mouth rinse containing a polyphosphate anticalculus agent and Triclosan, an antibacterial, antiplaque agent compatible therewith. The vehicle for these constituents is a water-alcohol mixture that includes a humectant. The total amount of water-alcohol in this preparation exceeds 70% by weight.

The Reed et al. U.S. Pat. No. 5,032,385 discloses an oral hygiene composition that includes Triclosan and polyethylene glycol. This patent points out that Triclosan, because of its lipophilic nature, tends to partition into a hydrophobic oil phase and a surfactant micellar phase and is therefore rendered unavailable for adsorption into the oral surfaces to be treated. By incorporating specified amounts of polyethylene glycol into the composition, the oral availability of the Triclosan can be maintained at an effective level.

SUMMARY OF INVENTION

In view of the foregoing, the main object of this invention is to provide an antiplaque mouth rinse whose composition includes two antibacterial agents which when used alone have limited effectiveness, but which when combined coact to promote the delivery to and the retention of these agents in the mouth and soft tissues in the dental region of the oral cavity, thereby enhancing the antibacterial activity inhibiting the development of plaque.

More specifically, an object of this invention is to provide a mouth rinse of the above type in which one of the antibacterial agents is Triclosan and the other, cetyl pyridinium chloride or another cationic antibacterial agent, which together give rise to enhanced antibacterial activity highly effective against the formation of plaque.

Also an object of this invention is to provide an antiplaque mouth rinse which is free of toxic agents and is pleasant tasting to render it acceptable to a typical user.

Briefly stated, these objects are attained in an antiplaque mouth rinse conducive to oral hygiene. The mouth rinse composition includes a water-alcohol vehicle having dissolved therein two antibacterial agents that coact to promote the delivery of these agents and their retention on the teeth and soft tissue in the dental region of the oral cavity of the user, thereby inhibiting the formation of plaque.

One agent, Triclosan, is water-insoluble and noncationic, a solubilizer therefor being included in the composition. The other agent, cetyl pyridinium chloride (CPC) is soluble in water and alcohol and is cationic. When the combination of Triclosan and CPC is delivered to the dental region, it is adsorbed and retained thereby to afford enhanced antibacterial activity.

DETAILED DESCRIPTION OF INVENTION

In an antiplaque mouth rinse in accordance with the invention, the vehicle or carrier for delivering the active antibacterial constituents to the dental region in the oral cavity of the user is a water-alcohol mixture in which the ratio of water to alcohol is about 4 to 1 by weight to about 6 to 1. The water is preferably de-ionized, and the alcohol, which must be non-toxic in nature, is preferably ethanol or grain alcohol, although isopropanol is also usable. Thus the amount of water by weight in the mouth rinse may be about 67% and the amount of alcohol, about 18%.

Also included in the mouth rinse composition is a humecant having an affinity for water and a stabilizing effect thereon. A preferred humectant is sorbitol in a 70% aqueous solution. The amount of sorbitol included in the formulation is preferably between about 10 to 15% by weight.

In the mouth rinse in accordance with the invention, two antibacterial agents are included, which by themselves, as indicated in the prior art, have limited effectiveness in combating the formation of plaque, but which when combined in the rinse coact to promote their delivery to and retention on the teeth and soft tissue in the dental region of the oral cavity and thereby strongly inhibit the formation of plaque.

Water-insoluble, non-cationic antibacterial agents, which are particularly desirable in terms of antiplaque effectiveness and safety, are halogenated diphenyl ethers, preferably Triclosan. In the present mouth rinse composition, an effective amount of Triclosan is included, typically about 0.01 to 0.05% by weight, preferably 0.03%.

Triclosan is substantially water-insoluble, meaning that its solubility is less than about 1% by weight in water at 25° C. Hence the composition must include a solubilizer for the Triclosan which does not adversely affect its antibacterial activity. The amount of the solubilizer may be between about 0.5 to 2.0% by weight, and must be sufficient to solubilize the water-insoluble Triclosan. A preferred solubilizer for this purpose is TWEEN 20 manufactured by Atlas Chemical Industries, Inc. TWEEN is the trademark for polyoxyethylene derivatives of fatty acid partial esters of sorbital anhydrides that are generally soluble in water.

The second antibacterial agent included in the mouth rinse is cetyl pyridinium chloride (CPC), which is the monohydrate of the quarternary salt of pyradine and cetyl chloride. CPC, which is cationic, is highly soluble in water and alcohol. The percentage by weight of CPC in the mouth rinse is in the range of about 0.020 to 0.030%, preferably about 0.025%, so that the amount by weight of the antibacterial agent in the formulation is almost equal to that the Triclosan agent, which is non-cationic.

We have found that the combination of the cationic with the non-cationic antibacterial agents has two significant effects: the first being that the combined agents are readily adsorped in the dental region and retained on the teeth and soft tissue for a relatively prolonged period and are not released by saliva in the oral cavity.

The second effect is that these agents coact to afford enhanced antibacterial activity that is highly effective against plaque, particularly interproximal plaque that is not reachable by mechanical expedients.

Also included in the composition is a defoaming agent, such as Pluronic L64 manufactured by Wyandotte Chemicals Corporation, preferably in an amount of about 10% by weight. Pluronic is the trademark for polyoxyalkylene derivatives of propylene glycol.

A small amount of sodium saccharine, say, about 0.75% by weight, may be added to the mouth rinse. This sweetener is highly soluble in water and is many times sweeter than sugar, thereby imparting a pleasant taste to the mouth rinse.

The mouth rinse may also include an effective amount of an anti-caries agent soluble in water, such as sodium fluoride, which is compatible with the antibacterial agents. And also included in small amounts, about 0.1% by weight, are coloring agents such as FD&C BLUE #1 and FD&C YELLOW #5.

The selected cationic and non-cationic antibacterial agents are compatible with each other and together provide enhanced bacterial activity when delivered to and adsorped by the dental region of the oral cavity of the user where they function to combat the formation of plaque.

While CPC is the preferred water-soluble cationic antibacterial agent and provides distinct advantages, usable in place of CPC in combination with Triclosan are such water-soluble cationic antibacterial agents as chlorhexidine and domiphen bromide, a quaternary salt.

A two-component antibacterial composition in accordance with the invention is not limited in its utility to mouth rinse procedures in which the user takes a small amount of the rinse in his mouth and swishes it around to bathe the dental region, and then spits it out, the agents being adsorped and retained by the teeth and soft tissue.

In practice, the mouth rinse may also be used for subgingival irrigation, in which case the rinse is poured into the reservoir of a dental irrigation device, such as the well known WATER PIK device. This device ejects the rinse as a stream through a hand-held nozzle which directs the stream toward a subgingival region.

A rinse in accordance with the invention may also be used as an impregnant for filling hollow, synthetic fibers for the localized delivery of antibacterial agents to treat disease-active pockets of periodontitis.

As indicated by Morrison et al. in Journal Periodontal, February 1992, in an article entitled "Root Surface Characteristits Associated with Subgingival Placement of Monolithic Tetracycline-Impregnated Fibers," the use of such impregnated fibers dramatically changes the subgingival microbial flora and decreases clinical signs of inflammation. The advantage of using a two-component antibacterial agent, one non-cationic and the other, cationic, in accordance with the invention, in place of tetracycline lies in the adsorption and retention characteristics of these combined agents and their enhanced antimicrobial activity at the diseased site.

It is also now known to implant drug-impregnated polymer wafers or other matrixes in various parts of the body to deliver drugs that cannot be delivered by mouth or through the skin. The polymer used for the wafer is one that is biodegradable and acts to release the impregnant as the wafer gradually dissolves. Such wafers may be impregnated with a two-component antibacterial composition in accordance with the invention, thereby slowly releasing this composition into a site to be treated over a prolonged period.

While there have been disclosed and described preferred compositions of an antiplaque mouth rinse in accordance with the invention, it will be appreciated that many changes and modifications may be made therein without, however, departing from the essential spirit thereof. Thus the composition may be applied to a dental floss in fluid or in gel form.

I claim:

1. A bactericidal composition for treating diseased tissues which consists essentially of:
   A. a first antibacterial agent constituted by an antibacterial effective amount of Triclosan which is substantially water insoluble and non-cationic;
   B. an antibacterial effective amount of a second antibacterial agent which is cetyl pyridinium chloride.

2. A composition as defined in claim 1 wherein the composition comprises:
   A. a first antibacterial agent constituted by an antibacterial effective amount of about 0.01 to 0.05 wt % of Triclosan which is substantially water insoluble and non-cationic;
   B. an antibacterial effective amount of a second antibacterial agent which is about 0.020 to 0.03 wt % of cetylpyridiniumn chloride.

3. A dental floss to which has been applied a composition of claim 1.

4. In a mouthwash the improvement which consists essentially of using as an antibacterial agent:
   A. a first antibacterial agent constituted by an antibacterial effective amount of Triclosan which is substantially water insoluble and non-cationic;
   B. an antibacterial effective amount of a second antibacterial agent which is cetylpyridinium chloride.

5. A antibacterial composition consisting essentially of Triclosan and a antibacterial agent which is a soluble cationic agent.

6. A antibacterial composition as defined in claim 5 wherein the cationic compound is cetyl pyridium chloride.

* * * * *